United States Patent [19]

McDonnell et al.

[11] Patent Number: 4,668,811

[45] Date of Patent: May 26, 1987

[54] DITHIENE DERIVATIVE

[75] Inventors: Damien G. McDonnell, Malvern; Paul F. Gordon, Rochdale; Anthony J. Hughes, Malvern Link; David J. Thompson, Whitefield, all of England

[73] Assignee: Imperial Chemical Industries PLC

[21] Appl. No.: 635,162

[22] Filed: Jul. 27, 1984

[30] Foreign Application Priority Data

Jul. 28, 1983 [GB] United Kingdom ............... 8320389
Aug. 31, 1983 [GB] United Kingdom ............... 8323359
Mar. 20, 1984 [GB] United Kingdom ............... 8407246

[51] Int. Cl.$^4$ .................. C07F 15/00; C07F 15/04
[52] U.S. Cl. ................................................. 556/146
[58] Field of Search ................ 260/439 R, 429 R; 556/146

[56] References Cited

U.S. PATENT DOCUMENTS 3,398,167  8/1968  Mahler ........................... 260/429 R
3,875,199  4/1975  Bloom ............................ 260/429 R
4,239,843 12/1980  Hara et al. ................... 260/439 R X
4,508,655  4/1985  Sasagawa et al. ............. 260/429 R

FOREIGN PATENT DOCUMENTS 1333808 10/1973 United Kingdom .

OTHER PUBLICATIONS

Engler et al., IBM Technical Disclosure Bulletin, V 20 (7), pp. 2858-2860 (1977).
Giroud et al., Mol. Cryst. Liq. Cryst. 56 (Letters), 1980, p. 225.
Research Disclosure No.: 21612, Apr. 1982, p. 117.
Schrauzer et al., JACS 87:07, Apr. 5, 1965, p. 1483.
Stiefel et al., JACS 87:13, Jul. 5, 1965, p. 3016.
Olsen et al., JACS 88:21, Nov. 5, 1966, p. 4876.
Schrauzer et al., JACS 92:19, 1970, p. 5769.
Vogler et al., Angew Chem. (Int. Ed.) 21 (1), 1982, p. 77.
Graczyk et al., Tetrahedron, vol. 38(17), 1982, p. 2715.
Nazzal et al., Trans. Metal Chem. 6, 1980, p. 318.
Reynolds et al., J. Appl. Physics, vol. 46(11), 1975, p. 4852.
Mueller-Westerhoff et al., JCS Chem. Comm., 1980, p. 497.
Mueller-Westerhoff et al., Mol. Cryst. Liq. Cryst. 56 (Letters), 1980, p. 249.

Primary Examiner—Helen M. S. Sneed
Attorney, Agent, or Firm—Cushman, Darby & Cushman

[57] ABSTRACT

A metal dithiene of the formula:

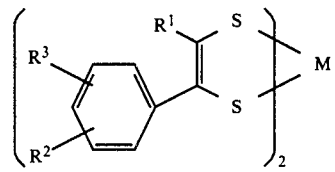

wherein
$R^1$ is $C_3$ to $C_{20}$ alkyl;
$R^2$ is selected from alkyl, alkylamino, dialkylamino, alkylthio and alkoxy in which each alkyl contains up to 20 carbon atoms;
$R^3$ is H, halogen or a group represented by $R^2$;
and M is a metal selected from Groups Ib, IIb, VIIb, and VIIIb of the Periodic Table, and a composition of the metal dithiene in a liquid crystal medium. The composition is suitable for use in a light valve for a laser-addressed liquid crystal display.

3 Claims, No Drawings

DITHIENE DERIVATIVE

This specification describes an invention relating to a dithiene derivative having an absorption band in the near infra-red region of the electromagnetic spectrum, e.g. 700-1300 nm, and more particularly in the region 750-900 nm, and to a composition of the derivative with a liquid crystal medium.

It is known that certain metal dithienes absorb in the infra-red region of the spectrum and are efficient converters of photochemical energy into thermal energy. This makes them potentially useful in switching applications, particularly in infra-red laser addressed systems such as liquid crystal light valves. However a disadvantage of the known metal dithienes is that they are not very soluble in organic solvents, particularly in liquid crystal media, and this has restricted their use in laser-addressed switching systems.

According to the present invention there is provided a compound of the formula:

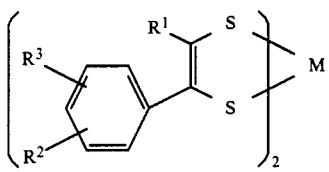

wherein $R^1$ is alkyl containing at least 3 carbon atoms;

$R^2$ is alkyl, alkylamino, dialkylamino, alkylthio or alkoxy;

$R^3$ is H, halogen or one of the groups represented by $R^2$ and M is a metal from Group Ib, IIb, VIIb, or VIIIb of the Periodic Table.

The alkyl group represented by $R^1$ desirably contains up to 20 carbon atoms, preferably from 4 to 12, and more preferably from 4 to 9, carbon atoms and may be branched or straight chain. When $R^3$ is H, the alkyl groups represented by, or contained in, $R^2$ preferably contain from 3 to 20 carbon atoms and more preferably from 4 to 12 carbon atoms and may be branched or straight chain and $R^2$ is preferably in a para-position on the benzene ring with respect to the bond linking the benzene ring to the dithiene nucleus. When $R^3$ is alkyl, the alkyl groups in $R^2$ and $R^3$ may contain up to 20 carbon atoms (branched or straight chain), but preferably contain from 1 to 12, and more preferably from 1 to 6, carbon atoms. $R^2$ and $R^3$ may be located anywhere on the benzene rings to which they are attached, but it is preferred that at least one is in a para-position in relation to the bond linking the benzene ring to the dithiene nucleus.

It is preferred that the metal represented by M is nickel, platinum or palladium but examples of other metal which may be suitable are cadmium, chromium, cobalt, copper, gold, iron, manganese and zinc.

The compound of Formula I may be prepared by the reaction of an aryl-alpha-bromo-ketone, carrying the appropriate groups $R^1$, $R^2$ and $R^3$, with a phosphorus sulphide, such as $P_2S_5$, followed by reaction with a salt of the metal. The first stage of the process is preferably performed in a polar solvent such as 1,4-dioxane or tetrahydrofuran at a temperature from 60° C. to 150° C., preferably 70° C., and conveniently under reflux. The second stage is conveniently performed by addition of an aqueous solution of the metal salt and heating at a similar temperature until reaction is complete. The product may be purified by, for example, recrystallisation and chromatograph methods.

Compounds in accordance with Formula I are more soluble in organic liquids, and especially in liquid crystal materials, than the equivalent compounds in which the groups attached to the dithiene nucleus are all alkyl, or all aryl or in which two of the groups are H, and this allows them to be used within a liquid crystal light valve, dissolved in a liquid being addressed by an infra-red laser. In the case of liquid crystal light valves this gives rise to improvements in speed of response and line which and also permits the ue of a lower power addressing laser.

According to a further feature of the present invention there is provided a composition comprising a liquid crystal material and a compound in accordance with Formula I.

The composition may comprise any of the recognised classes of liquid crystal material, e.g. nematic, cholesteric and smectic, but it is preferred to use a smectic liquid crystal material, such as S2 which is a mixture of cyano-biphenyls and cyano-terphenyls available from BDH Chemicals of Poole, Dorset, England.

The composition of the invention preferably contains from 0.1%, by weight, up to a level corresponding to the maximum solubility of the compound according to Formula I in the liquid crystal material at ambient temperatures. In many cases this maximum lies in the region from 5% to 10% by weight based upon the total weight of the composition. It is especially preferred that the composition contains at least 0.5% and more preferably at least 1% of the compound according to Formula I.

The composition of the present invention is useful in laser-addressed light valves.

The invention is further illustrated by the following Examples in which all parts and percentages are by weight unless otherwise indicated.

EXAMPLE 1

The compound of Formula I, in which M is Ni, $R^1$ is n—$C_7H_{15}$ $R^2$ is 4(n—$C_4H_9O$—) and $R^3$ is H, was prepared by refluxing 5.5 g of the aryl-alpha-bromo-ketone:

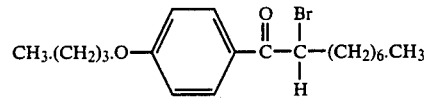

with 6.6 g of phosphorus pentasulphide in 25 g of 1,4-dioxan for 4 hours. The reaction mixture was then cooled and filtered and a solution of 1.43 g of nickel chloride hexahydrate in 7 g of water was added. The reaction mixture was then refluxed gently for a further 4 hours following which it was poured into water. The green oil which separated was purified on a silica column, eluting with a mixture of chloroform and hexane to give 2.53 g of a green crystalline solid, m.p. 67.5° C. A solution of the solid in chloroform has as a molar extinction coefficient of 25500 at the adsorption maximum of 826 nm. The solid has a solubility of 5%, by weight, at 20° C., in the liquid crystal medium E7, which is identified as Host 1 in U.K. Patent Specification No. 2,093,475.

The compounds of Formula I identified in Table 1, with their extinction coefficients ($\epsilon_{max}$) and absorption maxima ($\lambda_{max}$) in chloroform and their solubilities (Sol) in E7 at 20° C., were made by the process described in Example 1 using equivalent quantities of the appropriate aryl-alpha-bromo-ketone and metal chloride.

TABLE 1

| Ex | $R^1$ | $R^2$ | M | Sol (wt %) | $\epsilon_{max}$ | $\lambda_{max}$ (nm) |
|---|---|---|---|---|---|---|
| | $R^3$ = H | | | | | |
| 2 | —CH.CH$_2$.C(CH$_3$)$_3$ CH$_3$ | 4(—OC$_5$H$_{11}$) | Ni | >5 | 23000 | 823 |
| 3 | —(CH$_2$)$_6$.CH$_3$ | 4(—OC$_4$H$_9$) | Pt | >5 | 43500 | 776 |
| 4 | —(CH$_2$)$_4$.CH$_3$ | 4(—OC(CH$_3$)$_3$) | Ni | 5 | 24000 | 825 |
| 5 | —(CH$_2$)$_6$.CH$_3$ | 4(—C$_5$H$_{11}$) | Ni | >5 | 22500 | 812 |
| 6 | —(CH$_2$)$_6$.CH$_3$ | 4(—OC$_4$H$_9$) | Ni | | | |
| | $R^3$ = 3(—CH$_3$) | | | | | |
| 7 | —(CH$_2$)$_4$.CH$_3$ | 4(—CH$_3$) | Ni | >5 | 23000 | 808 |

Although E7 is a nematic liquid crystal material it is also a mixture of cyanobiphenyls and cyanoterphenyls and it has a similar solvent power to the smectic liquid crystal material S2 at a temperature above the smectic/nematic transition point. It is therefore more convenient to use for measuring the solubility of a compound of Formula I at room temperature because at this temperature E7 is fluid while S2 and similar smectic liquid crystal media are highly viscous.

Other compounds according to Formula I which can be made by the process of Example 1, using the appropriate metal chloride and aryl-alpha-bromo-ketone, are:

$R^1$ = —(CH$_2$)$_6$.CH$_3$, $R^2$ = 4(—N[C$_4$H$_9$]$_2$), $R^3$ = H & M = Ni $R^1$ = —(CH$_2$)$_6$.CH$_3$, $R^2$ = 4(—N[C$_4$H$_9$]$_2$), $R^3$ = H & M = Pt

We claim:
1. A compound of the formula:

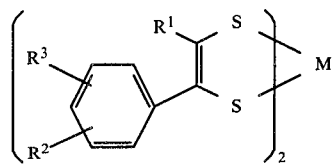

wherein $R^1$ is n-heptyl; $R^2$ is 4-n-butoxy; $R^3$ is H and M is nickel.

2. A compound of the formula:

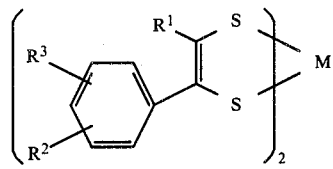

wherein $R^1$ is n-heptyl; $R^2$ is 4-n-butoxy; $R^3$ is H and M is platinum.

3. A compound of the formula:

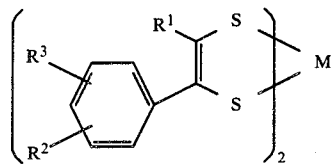

wherein $R^1$ is n-pentyl; $R^2$ is 4-methyl; $R^3$ is 3-methyl and M is nickel.

* * * * *